(12) United States Patent
Erzberger

(10) Patent No.: US 11,510,678 B2
(45) Date of Patent: Nov. 29, 2022

(54) SELF-EXPANDING VENTRICULAR PARTITIONING DEVICE INCLUDING ANCHOR

(71) Applicant: St. Jude Medical, Cardiology Division, Inc., St. Paul, MN (US)

(72) Inventor: Gary Erzberger, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 152 days.

(21) Appl. No.: 16/353,863

(22) Filed: Mar. 14, 2019

(65) Prior Publication Data
US 2019/0282238 A1    Sep. 19, 2019

Related U.S. Application Data

(60) Provisional application No. 62/643,251, filed on Mar. 15, 2018.

(51) Int. Cl.
*A61B 17/12*    (2006.01)
*A61B 17/00*    (2006.01)

(52) U.S. Cl.
CPC .... *A61B 17/1204* (2013.01); *A61B 17/12122* (2013.01); *A61B 17/12168* (2013.01); *A61B 2017/00243* (2013.01); *A61B 2017/00867* (2013.01)

(58) Field of Classification Search
CPC .......... A61B 17/1204; A61B 17/12122; A61B 17/12168; A61B 2017/00867; A61B 2017/00243; A61B 17/12172; A61B 2017/0427; A61B 2017/0464; A61B 2017/0417
See application file for complete search history.

(56) References Cited

U.S. PATENT DOCUMENTS

| 9,808,253 | B2 * | 11/2017 | Li .................... | A61B 17/12122 |
| 2003/0220667 | A1 * | 11/2003 | van der Burg ..... | A61B 17/0057 606/200 |
| 2004/0034366 | A1 * | 2/2004 | van der Burg ........... | A61F 2/01 606/119 |
| 2007/0213578 | A1 * | 9/2007 | Khairkhahan ... | A61B 17/12122 600/16 |
| 2009/0099647 | A1 * | 4/2009 | Glimsdale ........ | A61B 17/12113 623/1.35 |

(Continued)

FOREIGN PATENT DOCUMENTS

| CN | 104352261 B | * | 2/2015 | ......... A61B 17/0057 |
| WO | WO-2016138713 A1 | * | 9/2016 | ............. A61B 17/12 |
| WO | WO20160138713 | * | 9/2016 | ............. A61B 17/12 |

OTHER PUBLICATIONS

WO-2016138713 in Original Language with Paragraph Numbers, Sep. 2016, Pu Zhongjie from Patent Scope Website. (Year: 2016).*

(Continued)

*Primary Examiner* — Tuan V Nguyen
(74) *Attorney, Agent, or Firm* — Armstrong Teasdale LLP

(57) ABSTRACT

A ventricular partitioning device for isolating damaged tissue within a ventricle of the heart is disclosed. The ventricular partitioning device includes a disk-shaped portion configured to isolate a portion of a ventricular wall to facilitate remodeling of the ventricular wall. The device further includes an anchor configured to secure the device to the ventricular wall.

14 Claims, 9 Drawing Sheets

(56) References Cited

U.S. PATENT DOCUMENTS

| | | | | |
|---|---|---|---|---|
| 2010/0023048 A1* | 1/2010 | Mach | ............... | A61B 17/12177 |
| | | | | 606/200 |
| 2013/0165965 A1* | 6/2013 | Carlson | ............ | A61B 17/12122 |
| | | | | 606/213 |
| 2014/0179993 A1* | 6/2014 | Alexander | ............ | A61F 2/2487 |
| | | | | 600/37 |

OTHER PUBLICATIONS

WO-2016138713 translated to English with Paragraph Numbers, Sep. 2016, Pu Zhongjie from Patent Scope Website. (Year: 2016).*
Mazzaferri et al. "Percutaneous left ventricular partitioning in patients with chronic heart failure and a prior anterior myocardial infarction: Results of the Percutaneous Ventricular Restoration in Chronic Heart failure Patients Trial", American Heart Journal, 183(5): 812-821.

* cited by examiner

SELF-EXPANDING VENTRICULAR PARTITIONING DEVICE INCLUDING ANCHOR

CROSS-REFERENCE TO RELATED APPLICATIONS

This application claims the benefit of priority to U.S. Provisional Application No. 62/643,251, filed Mar. 15, 2018, which is incorporated by reference in its entirety herein.

BACKGROUND OF THE DISCLOSURE a. Field of the Disclosure

The present disclosure relates generally to medical devices for treating heart disease including congestive heart failure. In particular, various embodiments are directed to medical devices and methods for isolating damaged tissue within the heart, and specifically damaged tissue within the left ventricle of the heart.

b. Background Art

Myocardial infarction can cause ventricular hypertrophy and reduced cardiac stroke volume, which can lead to heart failure symptoms. These heart failure symptoms may include congestive heart failure that is characterized by a progressive enlargement of the heart, and particularly the left ventricle. As an individual's heart enlarges, it cannot efficiently pump blood forward with each heartbeat. Over time, the heart becomes ineffective as a pump and cannot adequately supply blood to the body. Further, as the heart enlarges, the internal heart valves such as the mitral valve cannot adequately close. An incompetent mitral valve allows regurgitation of blood from the left ventricle back into the left atrium, further reducing the heart's ability to pump blood forwardly and effectively.

Substantial effort has been made to find treatments for congestive heart disease. Surgical procedures have been developed to dissect and remove weakened or damaged portions of the ventricular wall in order to reduce heart volume. Additionally, mechanical assist devices have been developed as intermediate procedures for treating congestive heart disease. Such devices include left ventricular assist devices and total artificial hearts. More recently, improvements have been made in treating congestive heart failure by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta.

SUMMARY OF THE DISCLOSURE

The present disclosure is directed to a medical device. The medical device includes a disk-shaped portion having a distal end and a proximal end and configured to isolate a portion of a ventricular wall. The disk-shaped portion has a contracted state when constrained within a delivery device and a preset, expanded state when deployed from the delivery device. The medical device further includes an anchor coupled to the distal end of the disk-shaped portion and configured to secure the medical device to the ventricular wall.

The present disclosure is also directed to a method of delivering a medical device for isolating a portion of a ventricular wall of an individual. The method includes: (i) inserting a delivery device having the medical device disposed therein through an access path to a target site in a left ventricle of an individual; (ii) deploying partially the medical device to expose an anchor of the medical device; (iii) securing the anchor of the medical device to the ventricular wall; (iv) deploying the medical device to expose a disk within the left ventricle; (v) removing the delivery device; and (vi) uncoupling a delivery cable from the medical device.

The present disclosure is further directed to a method of delivering a medical device for isolating a portion of a ventricular wall of an individual. The method includes: (i) creating a hole in a left ventricular apex of the heart of the individual; (ii) inserting a delivery device having the medical device disposed therein into an access path to a target site adjacent the left ventricular apex of the heart; (iii) inserting the delivery device through the hole in the left ventricular apex of the heart and into a left ventricle of the individual; (iv) deploying partially the medical device to expose a disk within the left ventricle; (v) retracting the delivery device back through the hole in the left ventricular apex of the heart and out of the left ventricle; (vi) deploying fully the medical device to expose an anchor of the medical device; (vii) removing the delivery device; and (vii) uncoupling a delivery cable from the medical device.

The present disclosure is further directed to a method of delivering a medical device for isolating a portion of a ventricular wall of an individual. The method includes: (i) creating a hole in a left ventricular apex of the heart of the individual; (ii) inserting a delivery device having the medical device disposed therein into an access path to a target site in the left ventricle proximate the left ventricular apex of the heart; (iii) inserting the delivery device through the hole in the left ventricular apex of the heart until at least a portion of the delivery device extends completely through the hole in the left ventricular apex of the heart; (iv) deploying partially the medical device to expose an anchor of the medical device; (v) retracting the delivery device back through the hole in the left ventricular apex of the heart and into the left ventricle; (vi) deploying fully the medical device to expose a disk within the left ventricle; (vii) removing the delivery device; and (viii) uncoupling a delivery cable from the medical device.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
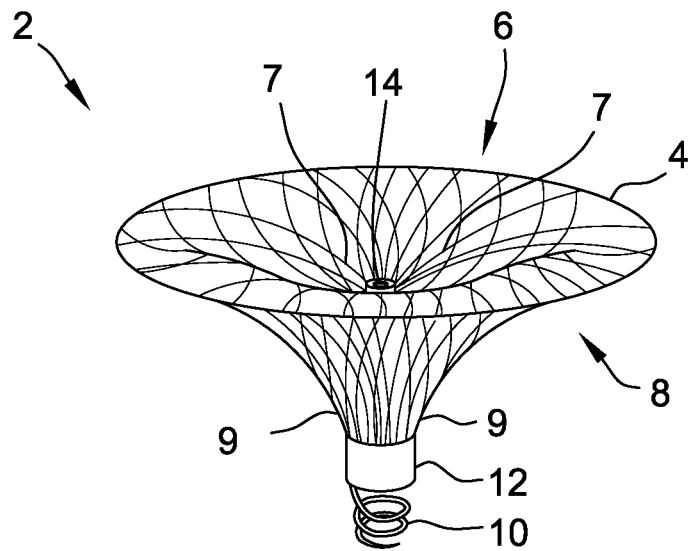
FIG. 1 is a perspective view of a ventricular partitioning device in accordance with one embodiment of the present disclosure.

Ventricular partitioning devices of the present disclosure are particularly suitable for use in individuals that have ventricular hypertrophy and resulting reduced cardiac stroke volume which, in many cases, are the direct result of a cardiac event such as a myocardial infarction. The ventricular partitioning devices described herein are suited to isolate damaged tissue along one or more areas of the ventricular wall to promote healing and remodeling of the ventricle. These devices provide a protective cover for the damaged tissue area and act to ease the pressure on the damaged cells. By partitioning the ventricle with the devices of the present disclosure, blood pumped is a higher percentage of the volume of the ventricle, thus increasing overall cardiac output. Further, the ventricular partitioning devices as described herein may be introduced into an individual through any number of access paths such as, for example, a femoral vein, a femoral artery, a carotid artery, or via ventricular apex access (though a minithoracotomy, for example). In many embodiments, the disclosed ventricular partitioning devices are particularly suitable for use within the left ventricle of an individual.

The ventricular partitioning devices made in accordance with the present disclosure are self-expanding and are particularly well suited for delivery through a catheter, delivery sheath, or the like to the left ventricle in an individual's heart. As noted, this allows damaged tissue on the ventricular wall to be isolated and protected to allow healing. The devices are configured such that they may be anchored at a single location near the left ventricular apex in many embodiments.

The ventricular partitioning devices provide a number of significant advantages to improve overall patient outcomes from procedures. As described more fully herein, these devices are self-expanding medical devices that do not require balloon inflation or other activation. This feature allows the devices in many embodiments to be easily recaptured and redeployed in the event that the positioning of the device and/or the sizing of the device is not optimal. Further, in many embodiments, the devices of the present disclosure can be loaded by a single pull into an introducer and do not require additional cables for collapsing the device during loading, thus simplifying loading and delivery of the devices. Additionally, the medical devices of the present disclosure have active anchoring at or near the ventricular apex (as opposed to anchoring at the top of the device along the ventricular wall) that is independent of the isolating function. This active anchoring enables the ventricular partitioning device to be fully placed before assessing performance and repositioning, and also ensures that the device will not embolize during or post-procedure. In many embodiments the active anchoring is at or near the left ventricular apex, and may either be internal or external the left ventricular apex.

Accordingly, the present disclosure is directed to a self-expanding ventricular partitioning device for isolating a portion of a ventricular wall, such as a portion of the left ventricular wall, which has been damaged due to a cardiac event or series of events. The device is configured to self-expand (upon deployment) into a preset expanded state from a contracted state when constrained within a delivery device, such as a delivery catheter, sheath, or introducer. As such, devices of the present disclosure are particularly suitable for delivery through a femoral vein trans-catheter procedure. Alternatively, the devices are also suitable for delivery through trans-catheter apical access, or other access paths.

The ventricular partitioning devices described herein include a disk-shaped portion having a distal end and a proximal end and are sized and configured to isolate a portion of the ventricular wall. The disk-shaped portion is the portion of the medical device that isolates and covers the damaged tissue on the ventricular wall to promote healing and remodeling of the ventricular tissue. The disk-shaped portion of the medical device is configured to be pliable and resilient in nature to provide the desired benefits. In some embodiments, all or a part of the disk-shaped portion may include a membrane, covering, or coating thereon to provide additional benefits. In some embodiments, the membrane, covering, or coating may be sewn onto the disk-shaped portion and optionally held in place with one or more sutures. In other embodiments, the membrane, covering, or coating may be sprayed or otherwise affixed on the disk-shaped portion. In one specific embodiment, the membrane, covering, or coating may be constructed from a polyester material. Other materials may also be suitable.

The ventricular partitioning devices further include an anchor coupled to the disk-shaped portion via a securing mechanism or the like that may in some embodiments gather and secure distal strands of the disk-shaped portion. The anchor is sized and configured to secure the medical device to the ventricular wall, generally at or near the left ventricular apex as further discussed herein. A center member may be disposed on the disk-shaped portion of the device that may be configured to gather and secure proximal strands of the disk-shaped portion and further configured in some embodiments to engage a delivery device. Other members may also be present on the medical device for engaging a delivery device. Also, although generally described herein as a ventricular partitioning device formed from a braided material, one skilled in the art will appreciate that ventricular partitioning devices in accordance with the present disclosure may be formed from one or more non-braided materials as well.

Referring now to the Figures, FIG. 1 is a perspective view of a ventricular partitioning device 2 in accordance with one embodiment of the present disclosure. Ventricular partitioning device 2 includes disk-shaped portion 4 having proximal end 6 comprised of proximal strands 7 and distal end 8 comprised of distal strands 9. Ventricular partitioning device 2 is configured to isolate a first portion of a ventricular wall (not shown in FIG. 1), as discussed herein. Ventricular partitioning device 2 additionally includes anchor 10 coupled to distal end 8 via securing mechanism 12. Additionally, anchor 10 may secure distal strands 9. Anchor 10 is illustrated in FIG. 1 as a screw-type anchor. Center member 14 is disposed on proximal end 6 of disk-shaped portion 4 and is configured to engage a delivery device (not shown in FIG. 1). Additionally, center member 14 may secure proximal strands 7. Strands 7, 9 may be secured additionally or alternatively by any other means known in the art such as soldering or heat treatment. Further still, use of an inverted or sock-type braid may result in strand ends at only one end of the device and obviate the need for securing strands at the other end of the device.

Figure 2:
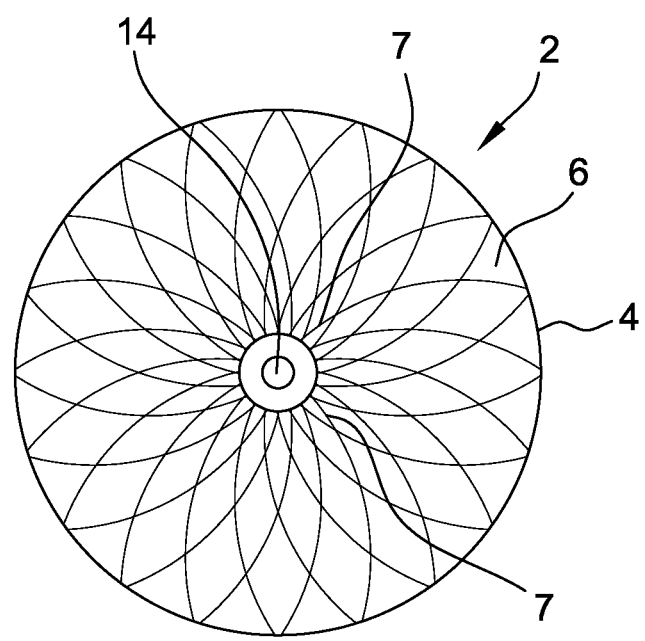
FIG. 2 is a top down view of the ventricular partitioning device of FIG. 1.

Referring now to FIG. 2, there is shown a top down view of ventricular partitioning device 2 of FIG. 1. FIG. 2 shows proximal end 6 of disk-shaped portion 4 comprised of proximal strands 7. FIG. 2 additionally shows center member 14 of ventricular partitioning device 2 located in the center of disk-shaped portion 4. Proximal strands 7 are secured by center member 14.

Figure 3:
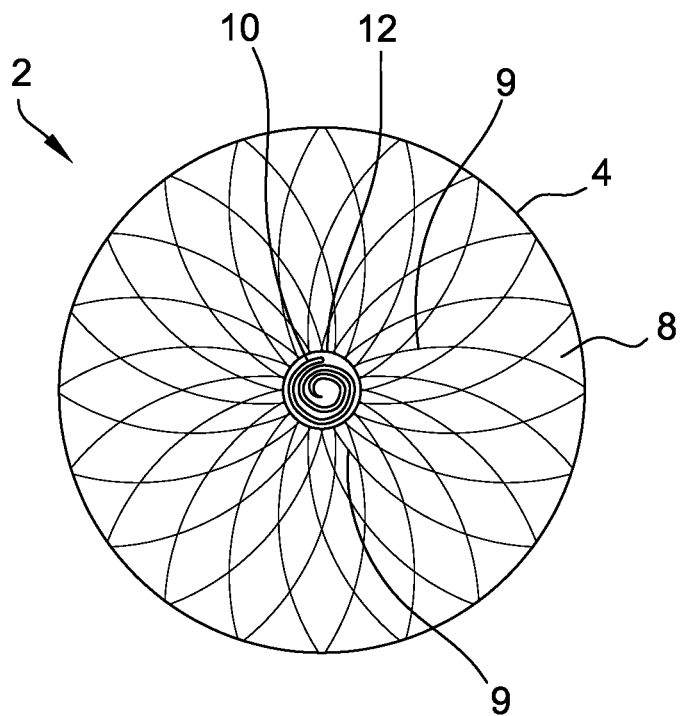
FIG. 3 is a bottom up view of the ventricular partitioning device of FIG. 1.

Referring now to FIG. 3, there is shown a bottom up view of ventricular partitioning device 2 of FIG. 1. FIG. 3 shows distal end 8 of disk-shaped portion 4 comprised of distal strands 9. FIG. 3 additionally shows anchor 10 and securing mechanism 12 of ventricular partitioning device 2 located in the center of disk-shaped portion 4. Distal strands 9 are secured by securing mechanism 12.

Ventricular partitioning device 2 may generally be formed from a plurality of strands that are braided together to form the desired structure, including disk-shaped portion 4, which may be formed of a single or multiple layers. As noted above, non-braided patterns and strands are also with the scope of the present disclosure. Although the strands are generally described as being braided, it is understood that according to additional embodiments of the present disclosure, ventricular partitioning device 2 may be formed by braiding, interweaving, knitting, or otherwise combining strands of materials together, such as by using a conventional braiding machine. These strand materials may include, for example, fibers, thread, yarn, cable, metallic wires, polymer monofilament or multifilament strands, and combinations of these materials, any of which are referenced herein as "strands," and such terms may be used interchangeably. The strands may be comprised of any material, such as natural materials, polymers, metals, metallic alloys, or combinations of the same. The strands may be braided to have a predetermined pick and pitch to define openings.

In one embodiment, the strands of ventricular partitioning device 2 may be form a metal fabric including a plurality of strands, such as two sets of essentially parallel generally helical strands, with the strands of one set having a "hand," or a direction of rotation, opposite that of the other set.

The pitch of the strands (the angle defined between the turns of the strands and the axis of the braid) and the pick of the fabric (the number of wire strand crossovers per unit length) may be adjusted as desired for a particular application. The wire strands of the metal fabric used in one embodiment may be formed of a material that is both resilient and can be heat treated to substantially set a desired shape. Materials which may be suitable for this purpose include a cobalt-based low thermal expansion alloy referred to in the field as Elgiloy, nickel-based high temperature high-strength "superalloys" commercially available from Haynes International under the trade name Hastelloy, nickel-based heat treatable alloys sold under the name Incoloy by International Nickel, and a number of different grades of stainless steel. An important consideration in choosing a suitable material for the wires strands is that the wires retain a suitable amount of the deformation induced by a molding surface when subjected to a predetermined heat treatment and elastically return to said molded shape after substantial deformation.

One class of materials which meets these qualifications is so-called shape memory alloys. One particular shape memory alloy that may be used is Nitinol. Nitinol alloys are also highly elastic and are said to be "superelastic," or "pseudoelastic." This elasticity may allow the device to return to a preset expanded configuration for deployment following passage in a distorted form through a delivery catheter. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed. One skilled in the art will also appreciate that other materials are suitable for formation of ventricular partitioning device 2 and are included within the scope of the present disclosure.

The anchor portion of the ventricular partitioning devices of the present disclosure acts to secure the devices to the ventricular wall, as discussed herein. In some embodiments of the present disclosure, the anchor will attach the ventricular partitioning device to the ventricular wall and extend partially into the ventricular wall at a desired location, such as proximate the left ventricular apex; that is, the anchor will penetrate into the ventricular wall tissue, but it will not completely penetrate through the ventricular wall to outside of the heart. In these embodiments, the ventricular partitioning device including the anchor is particularly suitable for deployment via a femoral vein trans-catheter procedure, for example. In other embodiments, the anchor will attach the ventricular partitioning device to the ventricular wall and extend from an inner surface of the ventricular wall to an outer surface of the ventricular wall at a desired location, such as proximate the left ventricular apex; that is, in these embodiments, the anchor extends completely through the ventricular wall generally at or near the left ventricular apex of the heart. In these embodiments, at least a portion of the anchor secures the ventricular partitioning device from a position exterior of the heart, generally near the left ventricular apex of the heart. When the anchor extends completely through the ventricular wall of the heart, the ventricular partitioning device is particularly suitable for deployment via a femoral vein trans-catheter procedure or by trans-catheter apex access from outside of the heart, for example.

The anchor portion of the ventricular partitioning device may be a screw-type anchor (See anchor 10 in FIG. 1) or may be a different type or form of anchor. When a screw-type anchor is used, the ventricular partitioning device is recapturable and repositionable; that is, a screw-type anchor may be removed and repositioned after insertion into the ventricular wall allowing for the ventricular partitioning device to be repositioned or removed from the body altogether. Screw-type anchors as disclosed herein provide excellent securement of the ventricular partitioning device to the ventricular wall while allowing for disengagement and repositioning of the medical device as needed. Ventricular partitioning devices of the present disclosure that include a screw-type anchor are suitable for delivery to the ventricle through a femoral vein trans-catheter procedure, for example. In many embodiments, the screw-type anchor may be constructed from stainless steel, or a like material, although other materials may be suitable as well.

Figure 4:
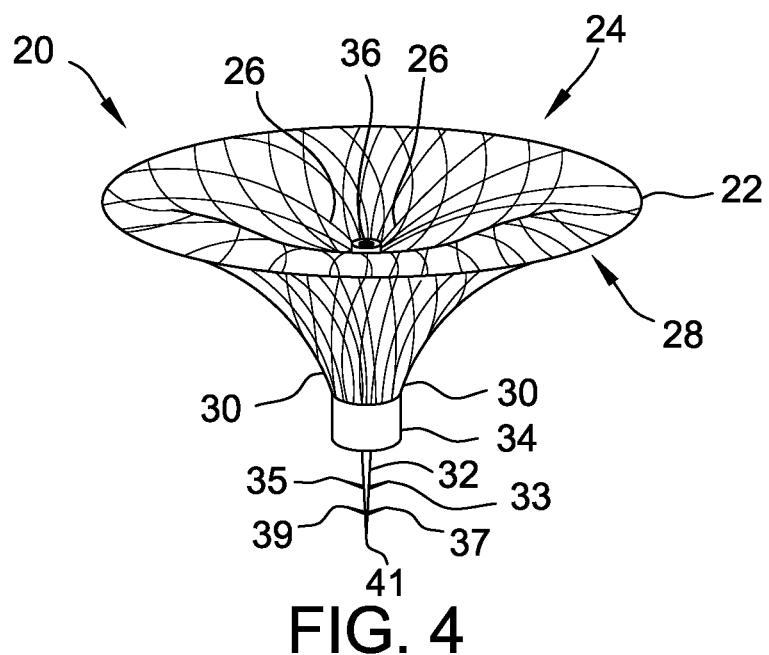
FIG. 4 is a perspective view of a ventricular partitioning device in accordance with another embodiment of the present disclosure.

Referring now to FIG. 4, there is shown a perspective view of a ventricular partitioning device 20 including an alternative anchor type in accordance with another embodiment of the present disclosure. Ventricular partitioning device 20 includes disk-shaped portion 22 having proximal end 24 comprised of proximal strands 26 and distal end 28 comprised of distal strands 30 and is configured to isolate a first portion of a ventricular wall, as discussed herein. Ventricular partitioning device 20 additionally includes anchor 32 coupled to distal end 28 via securing mechanism 34, which may secure ends of distal strands 30. Anchor 32 includes barbs 33, 35, 37, and 39 that extend radially outward and generally slightly upward to provide securement and gripping of tissue upon use while reducing the potential for disengagement from tissue. Anchor 32 further includes a sharp tip 41 for puncturing tissue for penetration of sharp tip 41 and barbs 33, 35, 37, and 39 into the ventricular wall. Center member 36 is disposed on proximal end 24 of disk-shaped portion 22 and is configured to engage a delivery device (not shown in FIG. 4) and may also secure ends of proximal strands 26. Ventricular partitioning devices including barb-type anchors as illustrated in FIG. 4 are particularly suitable for delivery to the ventricle through a femoral vein trans-catheter procedure, for example, and provide excellent securement of the medical device to the ventricular wall. In some embodiments, this type of anchor may be constructed from stainless steel, or a like material, although other materials may be suitable as well.

Figure 5:
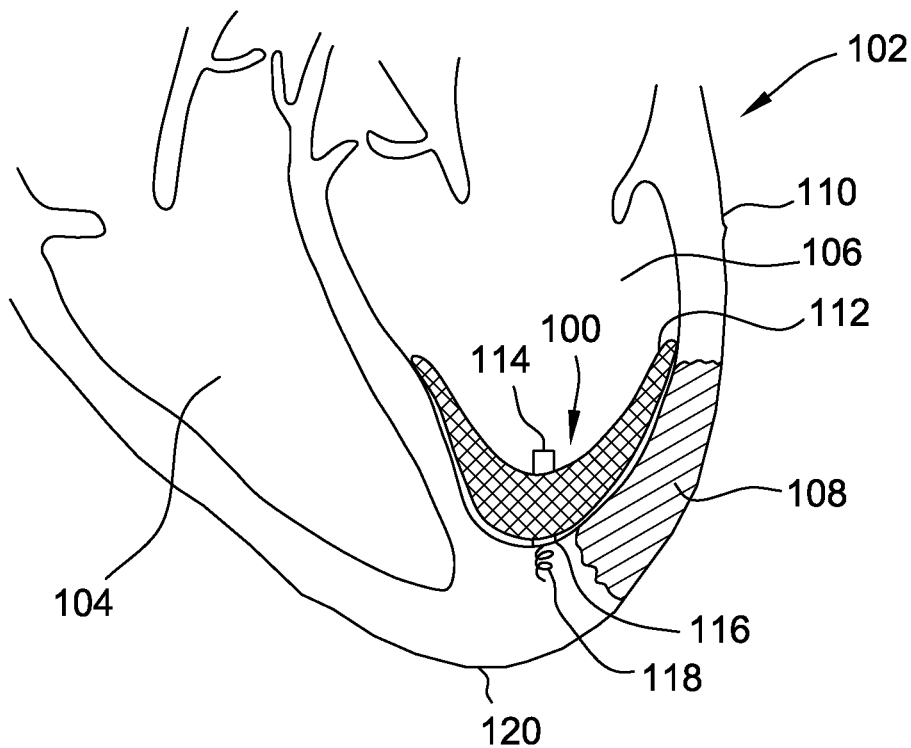
FIG. 5 illustrates a ventricular partitioning device positioned and anchored within the left ventricle of a heart.

Referring now to FIG. 5, there is shown one embodiment of a ventricular partitioning device 100 positioned and anchored within left ventricle 106 of heart 102. Heart 102 also includes right ventricle 104. Left ventricle 106 includes damaged tissue 108 on left ventricle wall 110 of left ventricle 106. Although not shown in FIG. 5, one skilled in the art will appreciate that damaged tissue may be present on one or more locations on left ventricle wall 110, and that damaged tissue may also be present on the wall between the left ventricle and the right ventricle. Ventricular partitioning device 100 includes disk-shaped portion 112, center member 114, securing mechanism 116 and screw-type anchor 118. As shown in FIG. 5, disk-shaped portion 112 of ventricular partitioning device 100 isolates damaged tissue 108 on left ventricle wall 110 such that pressure on damaged tissue 108 is reduced during heart contraction and healing may be promoted. Ventricular partitioning device 100 is anchored by screw-type anchor 118 to left ventricle wall 110 near left ventricular apex 120. As illustrated in FIG. 5, screw-type anchor 118 penetrates left ventricle wall 110 but does not extend entirely through left ventricle wall 110 to left ventricular apex 120. One skilled in the art will appreciate alternative anchor designs are equally possible to achieve this same result. Ventricular partitioning devices of the present disclosure that anchor into the left ventricle wall, but do not extend entirely through the left ventricle wall (see FIGS. 1, 4, and 5), are generally suitable for delivery to a target site through a vein, such as the femoral vein, of the individual, although other access paths may also be suitable.

Figure 6:
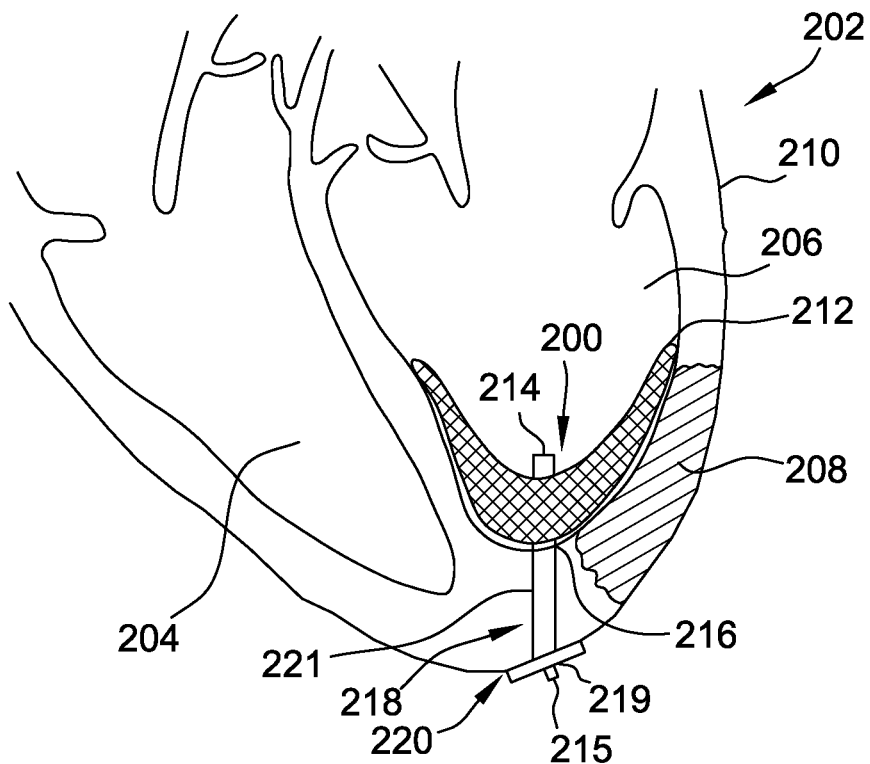
FIGS. 6-8 illustrate various ventricular partitioning devices positioned within the left ventricle of a heart and anchored through the ventricular wall proximate the left ventricular apex of the heart.
Figure 7:
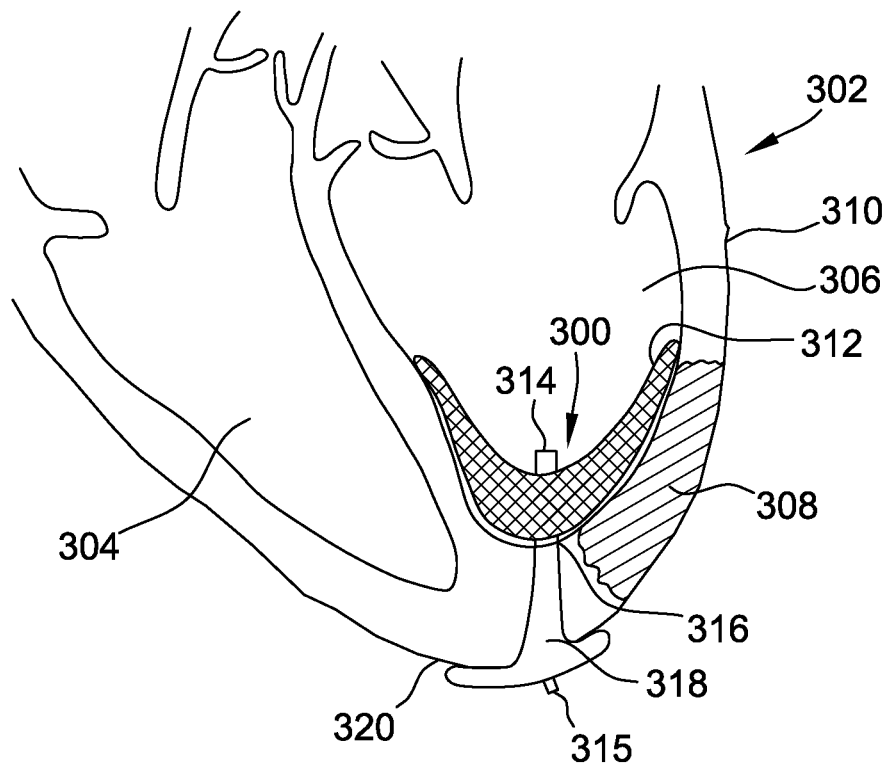
Figure 8:
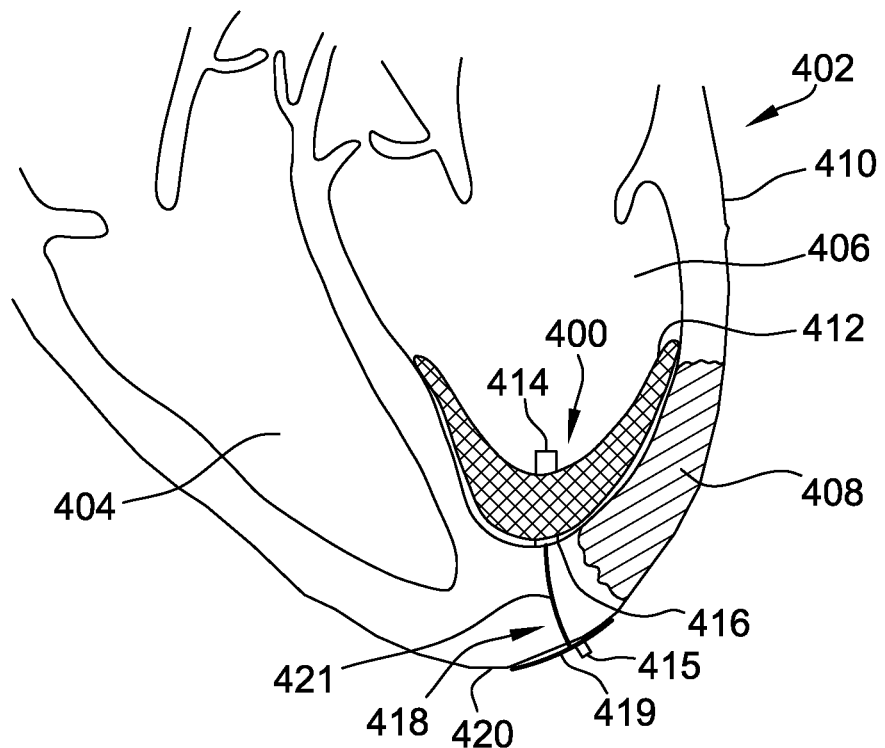

FIGS. 6-8 illustrate embodiments of the present disclosure where a ventricular partitioning device is deployed in the left ventricle of the heart and anchored through the ventricular wall proximate the left ventricular apex of the heart; that is, the embodiments illustrated in FIGS. 6-8 show an anchor portion of the ventricular partitioning device that extends completely through the ventricular wall and at least partially anchors the device from a position outside of the heart. FIG. 6-8 are simply intended to show exemplary embodiments of ventricular partitioning devices that include an anchor portion that extends exterior the heart and one skilled in the art based on the disclosure herein will understand that numerous alternative designs would also be suitable in many embodiments.

In these embodiments, at least a portion of the ventricular partitioning device, which may include a reduced diameter portion of the ventricular partitioning device, is placed into a hole or opening that extends through the ventricular wall. Generally, this hole or opening has been created by another medical device, although in some embodiments the hole or opening may be created by a delivery device that has the ventricular partitioning device disposed therein. In one specific embodiment, a hole or opening in the ventricular wall may be created by first inserting and routing a guidewire to the desired location along the ventricular wall and subsequently advancing a needle over the guidewire such that the needle tip contacts the ventricular wall. Using the needle tip and one or a series of dilators, a hole or opening of the desired size may be created in the ventricular wall. Other medical devices, including some delivery devices, may also be suitable for creating the hole or opening.

Referring now to FIG. 6, there is shown one embodiment of a ventricular partitioning device 200 positioned and anchored within left ventricle 206 of heart 202. Heart 202 also includes right ventricle 204. Left ventricle 206 includes damaged tissue 208 on left ventricle wall 210 of left ventricle 206. Ventricular partitioning device 200 includes disk-shaped portion 212, center members 214 and 215, securing mechanism 216 and plug-type anchor 218. Ventricular partitioning device 200 includes center members 214 and 215 which may allow a delivery device (not shown in FIG. 6) to engage ventricular partitioning device in separate locations for various delivery methods as further described herein. Although illustrated in FIG. 6 as having two center members that may engage a delivery device in some embodiments, one skilled in the art will recognize that ventricular partitioning device 200 may only include one center member in some embodiments. As shown in FIG. 6, disk-shaped portion 212 of ventricular partitioning device 200 isolates damaged tissue 208 on left ventricle wall 210. Ventricular partitioning device 200 is anchored by plug-type anchor 218 to left ventricle wall 210 near left ventricular apex 220. Plug-type anchor 218 includes a first anchor portion 219 configured for deployment adjacent left ventricular apex 220 (outside of heart 202) that is connected to a reduced diameter portion 221 configured to extend through left ventricle wall 210. Reduced diameter portion 221 is configured to pull or otherwise force first anchor portion 219 in a desired direction and to allow first anchor portion 219 to provide an anchoring function. As illustrated in FIG. 6, plug-type anchor 218 penetrates left ventricle wall 210 and extends entirely through left ventricle wall 210 proximate to left ventricular apex 220 where it provides an anchoring function. First anchor portion 219 of plug-type anchor 218 seats against left ventricular apex 220 and secures ventricular partitioning device 200 in place. Plug-type anchor 218 may be constructed from any suitable material substantially pliable to perform its intended function including, for example, a silicone-based material. Plug-type anchor 218 may be a single or multiple-piece design, and may be sized and configured to provide a desired anchoring function.

Referring now to FIG. 7, there is shown another embodiment of a ventricular partitioning device 300 positioned and anchored within left ventricle 306 of heart 302. Heart 302 also includes right ventricle 304. Left ventricle 306 includes damaged tissue 308 on left ventricle wall 310 of left ventricle 306. Ventricular partitioning device 300 includes disk-shaped portion 312, center members 314 and 315, securing mechanism 316 and self-expanding-type anchor 318. Ventricular partitioning device 300 includes center members 314 and 315 which may allow a delivery device (not shown in FIG. 7) to engage ventricular partitioning device in separate locations for various delivery methods as further described herein. Center members 314 and 315 may also act to secure strands in some embodiments. Although illustrated in FIG. 7 as having two center members that may be configured to engage a delivery device, one skilled in the art will recognize that ventricular partitioning device 300 may only include one center member in some embodiments.

As shown in FIG. 7, disk-shaped portion 312 of ventricular partitioning device 300 isolates damaged tissue 308 on left ventricle wall 310. Ventricular partitioning device 300 is anchored by self-expanding-type anchor 318 to left ventricle wall 310 near left ventricular apex 320 (outside of heart 302). Self-expanding-type anchor 318 is a self-expanding member that has a contracted state when constrained within a delivery device and a preset, expanded state when deployed from the delivery device. Self-expanding-type anchor 318 extends through ventricle wall 310. As illustrated in FIG. 7, self-expanding-type anchor 318 penetrates left ventricle wall 310 and extends entirely through left ventricle wall 310 proximate to left ventricular apex 320 where it provides an anchoring function. Self-expanding-type anchor 318 seats against left ventricular apex 320 and secures ventricular partitioning device 300 in place. Self-expanding-type anchor 318 may be constructed from any suitable material, including braided and non-braided fabrics as described herein.

Referring now to FIG. 8, there is shown another embodiment of a ventricular partitioning device 400 positioned and anchored within left ventricle 406 of heart 402. Heart 402 also includes right ventricle 404. Left ventricle 406 includes damaged tissue 408 on left ventricle wall 410 of left ventricle 406. Ventricular partitioning device 400 includes disk-shaped portion 412, center members 414 and 415, securing mechanism 416 and tethering-type anchor 418. Ventricular partitioning device 400 includes center members 414 and 415 which may allow a delivery device (not shown in FIG. 8) to engage ventricular partitioning device 400 in separate locations for various delivery methods as further described herein. Center members 414 and 415 may also act to secure strands in some embodiments. Although illustrated in FIG. 8 as having two center members that may be configured to engage a delivery device, one skilled in the art will recognize that ventricular partitioning device 400 may only include one center member in some embodiments.

As shown in FIG. 8, disk-shaped portion 412 of ventricular partitioning device 400 isolates damaged tissue 408 on left ventricle wall 410. Ventricular partitioning device 400 is anchored by tethering-type anchor 418 to left ventricle wall 410 near left ventricular apex 420. Tethering-type anchor 418 includes a positioning member 419 configured for deployment adjacent left ventricular apex 420 (outside of heart 402) and a tethering member 421 for coupling to disk-shaped portion 412 and extending through ventricle wall 410. As illustrated in FIG. 8, tethering-type anchor 418 penetrates left ventricle wall 410 and extends entirely through left ventricle wall 410 proximate to left ventricular apex 420 where it provides an anchoring function through positioning member 419. Tethering-type anchor 418 seats against left ventricular apex 420 and secures ventricular partitioning device 400 in place. Positioning member 419 may be cinched up tightly against left ventricular apex 420 using a clamping mechanism (not shown) or a ratcheting system (not shown) or other suitable method that allows disc-shaped portion 412 to be slid tighter in one direction for securement. In some embodiments, the tethering-type anchor may allow for a smaller diameter hole size in the ventricular wall.

As noted herein, the present disclosure is also directed to methods of delivering a medical device for isolating a portion of the ventricular wall of an individual. In particular, methods are disclosed herein for delivering a medical device for isolating a portion of the left ventricular wall of an individual to allow that portion of the ventricular to heal and/or rebuild. Some of the disclosed methods include anchoring the medical device by extending an anchor portion of the medical device partially into the ventricular wall (see FIG. 5). Other disclosed methods include anchoring the medical device by extending an anchor entirely through the ventricular wall such that part of the anchor is exterior the heart near or proximate the left ventricular apex of the heart (see FIGS. 6, 7, and 8). Additionally, some methods include inserting a delivery device having a medical device disposed therein through a vein (e.g., a femoral vein) or otherwise to a target site within the left ventricle while other methods include inserting a delivery device having a medical device disposed therein through a vein or otherwise to a target site near the left ventricular apex and inserting the delivery device into the left ventricle through a hole or opening in the left ventricular apex of an individual.

In one particular embodiment a method of delivering a medical device for isolating a portion of a ventricular wall of an individual includes first coupling a delivery cable to a medical device. The medical device comprises a disk-shaped portion having a distal end and a proximal end where the disk-shaped portion is configured to isolate a first portion of the ventricular wall. The disk-shaped portion has a contracted state when constrained within a delivery device and a preset, expanded state when deployed from the delivery device. The medical device also includes an anchor coupled to the distal end of the disk-shaped portion and configured to secure the medical device to the ventricular wall proximate the left ventricular apex. The method further includes elongating the medical device, which in many embodiments may be accomplished by a single pull, and inserting the medical device into a delivery device, delivery sheath, delivery catheter, or the like. In some embodiments of the present disclosure, the medical device may be prepared such that it is pre-loaded into a delivery device, delivery sheath, delivery catheter, or the like and attached to a delivery cable for use. The delivery device having the medical device disposed therein is then inserted through a vein (e.g., a femoral vein) or otherwise to a target site in the left ventricle proximate the left ventricular apex in the individual and the medical device partially deployed (unsheathed) from the delivery device to expose the anchor of the medical device. After the partial deployment to expose the anchor is complete, the anchor is secured to the ventricular wall at the target site (generally by screwing the anchor into the ventricular wall with a delivery cable if a screw-type anchor is used (see FIG. 1) or by pushing the anchor into the ventricular wall with a delivery cable if a barb-type anchor is used (see FIG. 4); in some embodiments, the delivery device may also be used to assist in the screwing or pushing of the anchor). After securing the medical device via the anchor to the left ventricular wall, the remaining portion of the medical device is deployed from the delivery device and the delivery device removed. The unsheathing of the remaining portion of the medical device from the delivery device allows the disk-shaped portion of the medical device to attain its preset, expanded state within the left ventricle, contact the left ventricle, and provide the isolation function described herein. Finally, the delivery cable is uncoupled from the medical device. Many embodiments including this method of delivery allow for the medical device to be recaptured, repositioned, and redeployed as desired.

Figure 9:
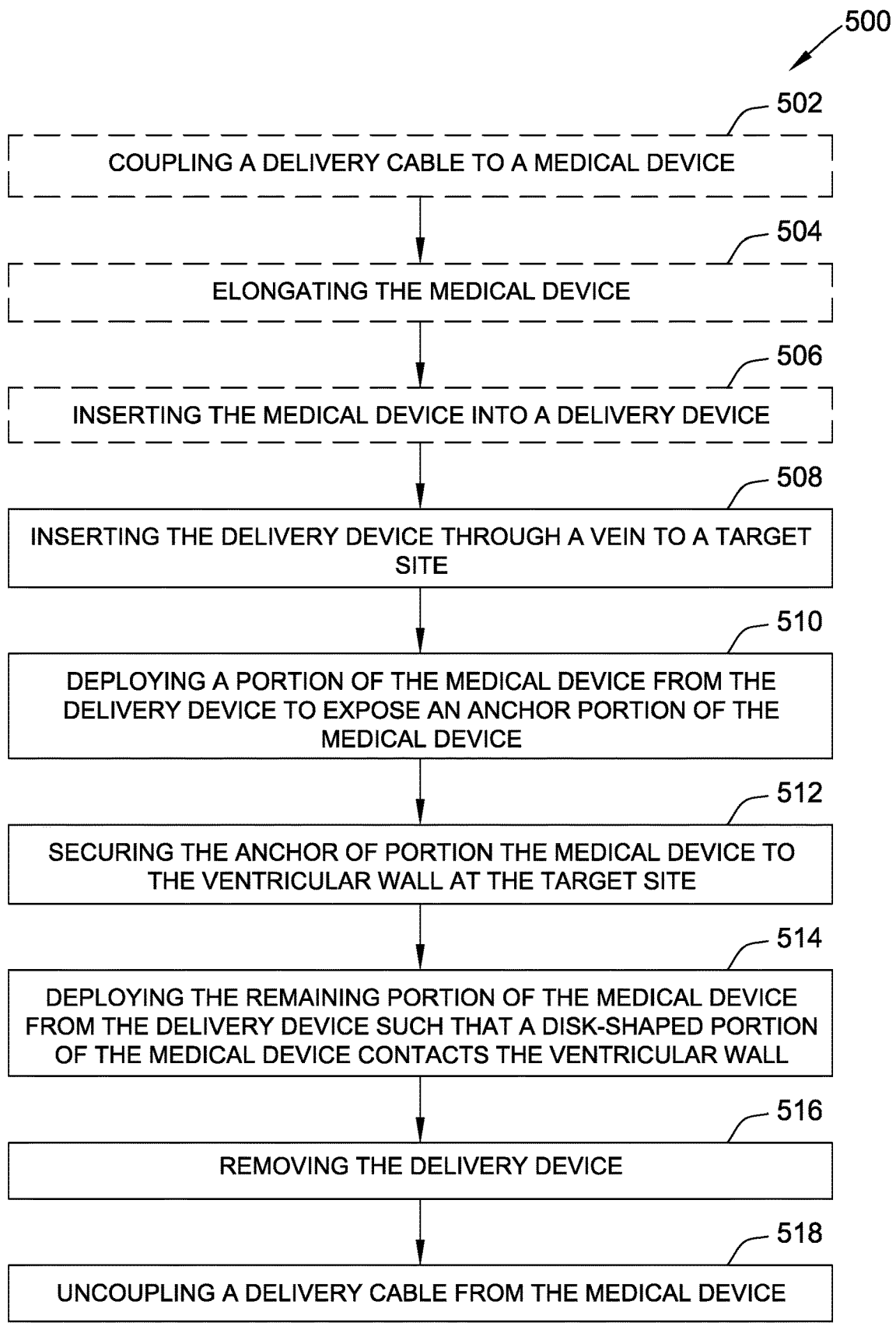
FIGS. 9, 10A, 10B, 11A, and 11B are flow diagrams of methods of delivering a medical device for isolating a portion of a ventricular wall of an individual.

FIG. 9 is a flow diagram of a method 500 of delivering a medical device for isolating a portion of a ventricular wall of an individual. Method 500 includes coupling 502 a delivery cable to the medical device. For example, as described above with reference to FIGS. 1-8, the medical device may comprise: (i) a disk-shaped portion configured to isolate a first portion of the ventricular wall, the disk-shaped portion having a contracted state when constrained within a delivery device and a preset, expanded state when deployed from the delivery device; and (ii) an anchor coupled to the disk-shaped portion and configured to secure the medical device to the ventricular wall proximate the left ventricular apex. The method further includes elongating 504 the medical device and inserting 506 the medical device into a delivery device. These initial steps (502-506) of method 500 are optional, for example when the medical device is "pre-loaded" within the delivery device.

Method 500 additionally includes inserting 508 the delivery device through a vein (e.g., femoral) to a target site proximate the ventricular apex in the individual and deploying 510 a portion of the medical device from the delivery device to expose an anchor on the medical device. Method 500 further includes securing 512 the anchor of the medical device to the ventricular wall at the target site and deploying 514 the remaining portion of the medical device from the delivery device such that the disk-shaped portion of the medical device contacts the ventricular wall. Finally, method 500 includes removing 516 the delivery device and uncoupling 518 the delivery cable from the medical device. While described above in one possible sequence, the steps of method 500 (and also the steps of methods 600 and 700 discussed below) may be altered and continue to perform the intended function (i.e. deployment of the medical device). For example, in some embodiments, uncoupling 518 the delivery device occurs prior to removal 516 of the delivery device.

In other embodiments of the present disclosure, there are disclosed methods of delivering a medical device for isolating a portion of a ventricular wall of an individual wherein the anchor portion of the medical device extends entirely through the ventricular wall; that is, with these methods, a hole or opening is first created in the left ventricular apex of the heart to allow a portion of the medical device (the anchor) to extend entirely through the ventricular wall and exterior of the heart to provide an anchoring function. As noted herein, this hole or opening may be created in some embodiments through the use of a needle and one or more dilators. Other embodiments may utilize one or more delivery devices or other medical devices to create the hole or opening. One skilled in the art will recognize that other suitable methods for creating the hole or opening in the left ventricular apex are also within the scope of the present disclosure.

In one specific method of the present disclosure where a medical device including an anchor that extends entirely through the ventricular wall is utilized, the medical device is delivered into the left ventricle from a hole created in the left ventricular apex of the heart. The hole is appropriately sized to allow a delivery device to pass therethrough. Once the hole is created, the method further includes optionally coupling a delivery cable to a medical device. The medical device comprises a disk-shaped portion having a distal end and a proximal end where the disk-shaped portion is configured to isolate a first portion of the ventricular wall. The disk-shaped portion has a contracted state when constrained within a delivery device and a preset, expanded state when deployed from the delivery device. The medical device also includes an anchor coupled to the distal end of the disk-shaped portion and configured to secure the medical device in the left ventricular apex of the heart. After coupling, the medical device is optionally elongated and inserted into a delivery device. In some embodiments of the present disclosure, the medical device may be prepared such that it is pre-loaded into a delivery device, delivery sheath, delivery catheter, or the like and attached to a delivery cable for use. In those embodiments, the coupling and elongation steps may be omitted. The delivery device having the medical device disposed therein is either inserted through a vein or otherwise (e.g. direct apical access during open heart surgery) to a target site adjacent the left ventricular apex of the heart (e.g. inserted distally through the hole and into the left ventricle of the individual). As noted, in some embodiments, the hole in the left ventricular apex may be created by a delivery device such that the delivery device creates the hole as the medical device is being delivered into the left ventricle.

Once the delivery device is inside of the left ventricle, a portion of the medical device is deployed to expose the disk-shaped portion such that the disk-shaped portion can expand to its preset, expanded state and contact the ventricular wall. Once the disk-shaped portion has been deployed and positioned against the ventricular wall, the delivery device is pulled back through the hole in the left ventricular apex and the remaining portion of the medical device is deployed such that the anchor extends through the ventricular wall and exterior the heart to provide the anchoring function. Once the medical device has been fully deployed and the anchor properly positioned, the delivery device is removed and the delivery cable is uncoupled from the medical device (or, these steps are reversed such that the delivery cable is uncoupled from the medical device prior to delivery device removal). In this embodiment, the disk portion of the medical device is deployed prior to the deployment of the anchor portion of the medical device.

Figure 10A:
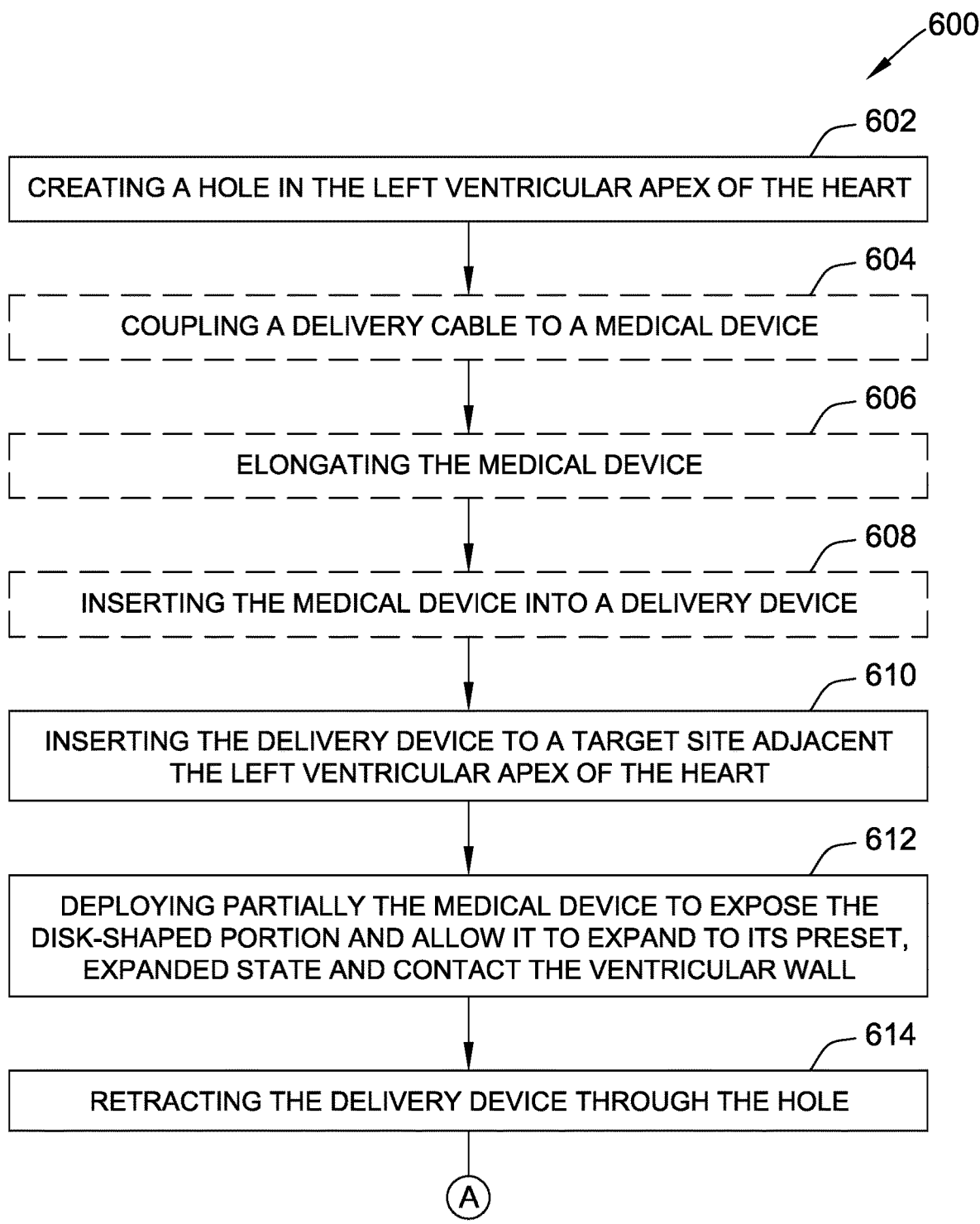
Figure 10B:
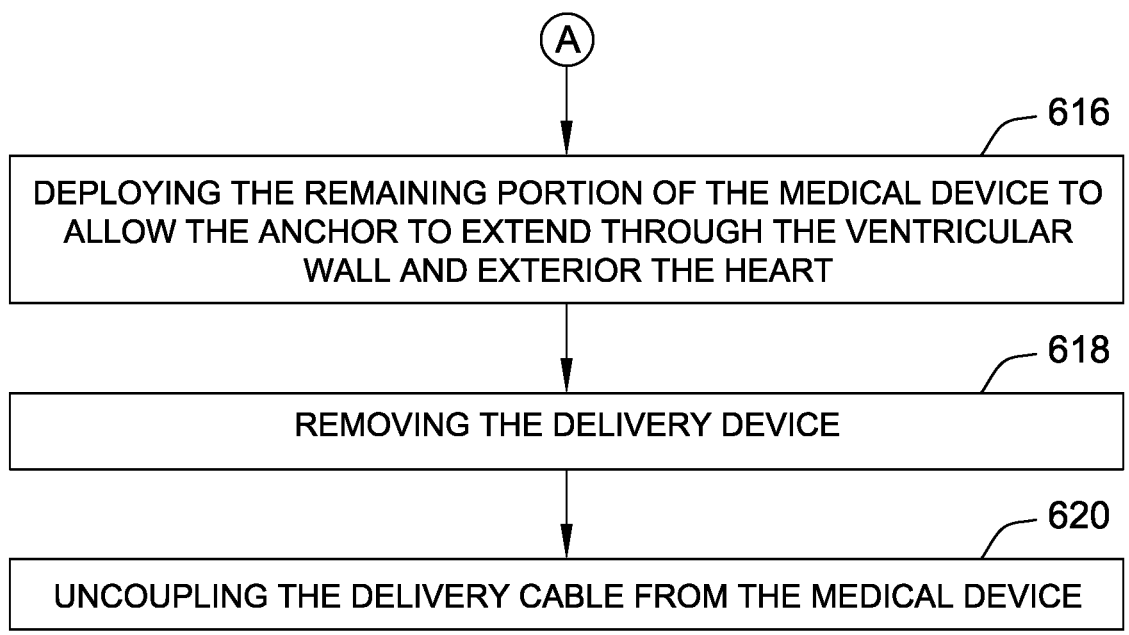

FIGS. 10A and 10B are a flow diagram of a method 600 of delivering a medical device for isolating a portion of a ventricular wall of an individual. Method 600 optionally includes creating 602 a hole in the left ventricular apex of the heart. Method 600 further includes coupling 604 a delivery cable to the medical device. For example, as described above with reference to FIGS. 1-8, the medical device may comprise: (i) a disk-shaped portion configured to isolate a first portion of the ventricular wall, the disk-shaped portion having a contracted state when constrained within a delivery device and a preset, expanded state when deployed from the delivery device; and (ii) an anchor coupled to the disk-shaped portion and configured to secure the medical device in the left ventricular apex of the heart. Method 600 further includes optionally elongating 606 the medical device and optionally inserting 608 the medical device into a delivery device. In instances where the medical device is "pre-loaded", steps 604-608 may be omitted.

Method 600 additionally includes inserting 610 the delivery device to a target site adjacent the left ventricular apex of the heart (e.g. introducing the delivery device through a vein to a location adjacent the hole or directly inserting the delivery device through the hole and into the left ventricle). Method 600 further includes partially deploying 612 the medical device to expose the disk-shaped portion and allow it to expand to its preset, expanded state and contact the ventricular wall. Method 600 additionally includes retracting 614 the delivery device through the hole and deploying 616 the remaining portion of the medical device to allow the anchor to extend thorough the ventricular wall and exterior the heart. Finally, method 600 includes removing 618 the delivery device and uncoupling 620 the delivery cable from the medical device. Alternatively, uncoupling 620 occurs prior to removal 618 of the delivery device.

In another specific method of the present disclosure where a medical device including an anchor that extends entirely through the ventricular wall is utilized, the medical device is delivered into the left ventricle through a vein (e.g., femoral vein) and the medical device is anchored exterior the heart using a hole created in the left ventricular apex of the heart as described above. The hole is appropriately sized to allow a delivery device to pass therethrough to deliver the anchor exterior the heart.

Once the hole is created in the left ventricular apex as described herein, the method further includes coupling a delivery cable to a medical device. The medical device comprises a disk-shaped portion having a distal end and a proximal end where the disk-shaped portion is configured to isolate a first portion of the ventricular wall. The disk-shaped portion has a contracted state when constrained within a delivery device and a preset, expanded state when deployed from the delivery device. The medical device also includes an anchor coupled to the distal end of the disk-shaped portion and configured to secure the medical device in the left ventricular apex of the heart. After coupling, the medical device is elongated and inserted into a delivery device. In some embodiments of the present disclosure, the medical device may be prepared such that it is pre-loaded into a delivery device, delivery sheath, delivery catheter, or the like and attached to a delivery cable for use rendering the steps of coupling and elongation unnecessary. The delivery device having the medical device disposed therein is then inserted through a vein or otherwise to a target site in the left ventricle proximate the hole created in the left ventricular apex. As noted, in some embodiments, the hole in the left ventricular apex may be created by a delivery device such that the delivery device creates the hole as the medical device is being delivered.

The delivery device is then inserted from the left ventricle into the hole until at least a portion of the delivery device has extended completely through the hole and exterior to the heart. Once at least a portion of the delivery device is exterior the heart (by extending through the hole created), the medical device partially deployed (unsheathed) from the delivery device to expose the portion of the anchor that secures the medical device exterior the heart. Once the anchor portion has been deployed, the delivery device is retracted back through the hole and back into the left ventricle where the remaining portion of the medical device is deployed to expose the disk-shaped portion such that the disk-shaped portion can expand to its preset, expanded state and contact the ventricular wall. Once the medical device has been fully deployed and the disk-shaped portion properly positioned, the delivery device is removed and the delivery cable is uncoupled from the medical device (or in reverse the delivery cable is uncoupled and the delivery device removed). In this embodiment, the anchor portion of the medical device is deployed exterior the heart prior to deployment of the disk portion within the left ventricle.

Figure 11A:
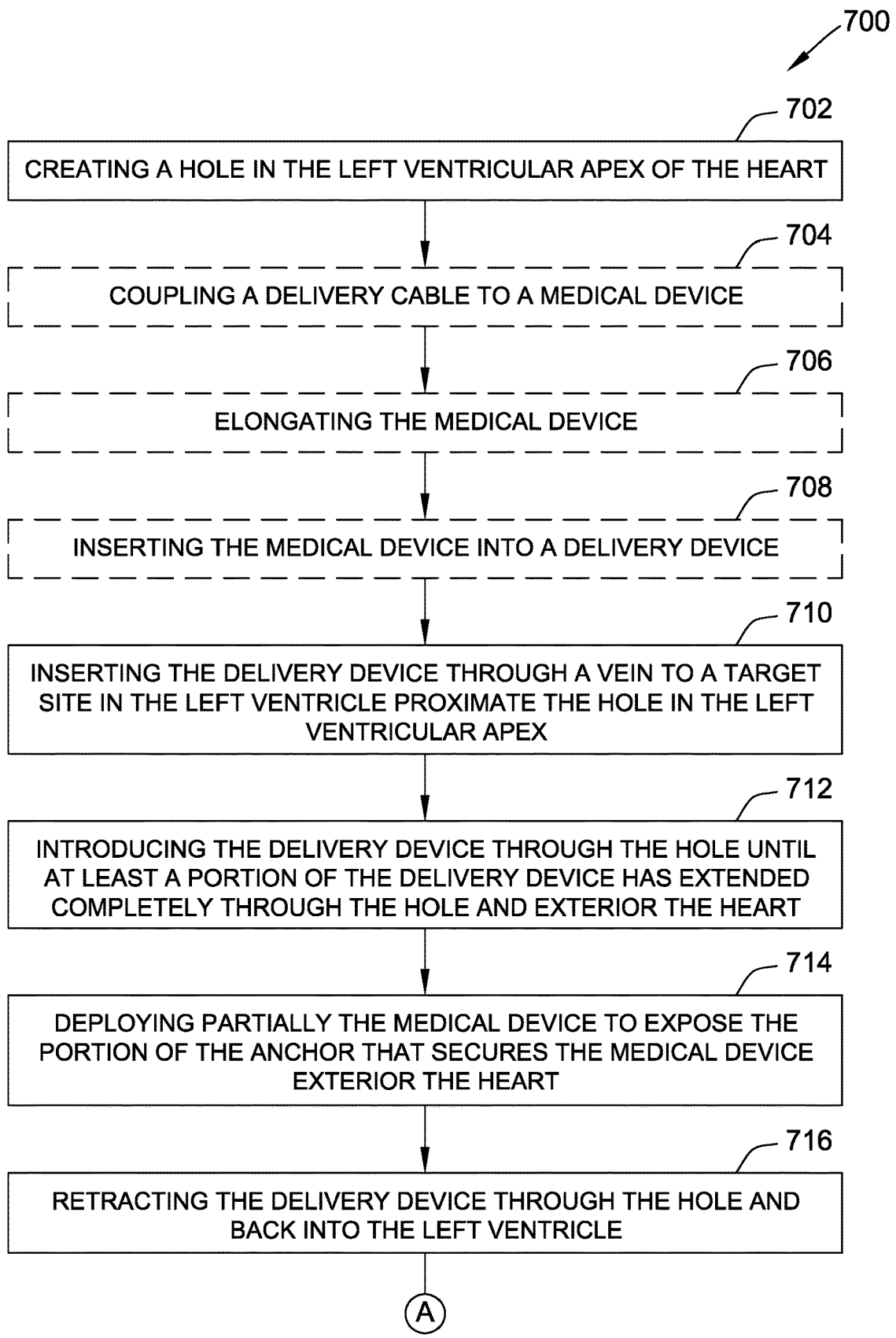
Figure 11B:
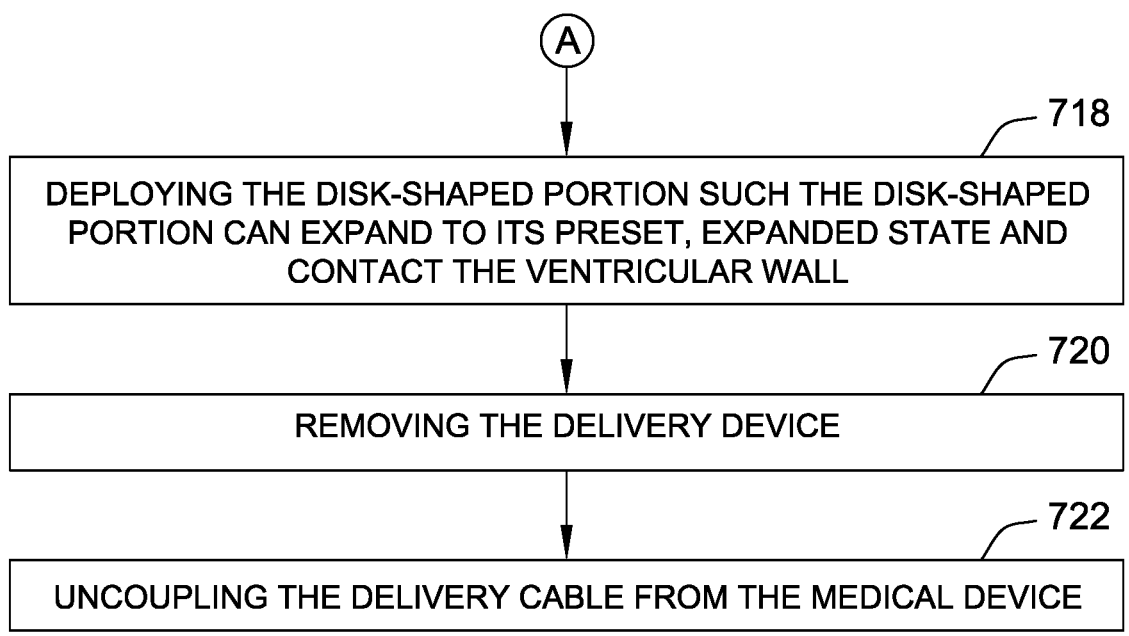

FIGS. 11A and 11B are a flow diagram of a method 700 of delivering a medical device for isolating a portion of a ventricular wall of an individual. Method 700 includes creating 702 a hole in the left ventricular apex of the heart. Method 700 optionally includes coupling 704 a delivery cable to the medical device. For example, as described above with reference to FIGS. 1-8, the medical device may comprise: (i) a disk-shaped portion configured to isolate a first portion of the ventricular wall, the disk-shaped portion having a contracted state when constrained within a delivery device and a preset, expanded state when deployed from the delivery device; and (ii) an anchor coupled to the disk-shaped portion and configured to secure the medical device in the left ventricular apex of the heart. Method 700 optionally includes elongating 706 the medical device and optionally inserting 708 the medical device into a delivery device. In embodiments where the device is "pre-loaded", steps 704-708 may be unnecessary.

Method 700 additionally includes inserting 710 the delivery device through a vein to a target site in the left ventricle proximate the hole in the left ventricular apex and inserting 712 the delivery device through the hole until at least a portion of the delivery device has extended completely through the hole and exterior the heart. Method 700 further includes partially deploying 714 the medical device to expose the portion of the anchor that secures the medical device exterior the heart. Method 700 additionally includes retracting 716 the delivery device through the hole and back into the left ventricle and deploying 718 the disk-shaped portion such that the disk-shaped portion can expand to its present, expanded state and contact the ventricular wall. Finally, method 700 includes removing 720 the delivery device and uncoupling 722 the delivery cable from the medical device.

Although a number embodiments of this disclosure have been described above with a certain degree of particularity, those skilled in the art could make numerous alterations to the disclosed embodiments without departing from the spirit or scope of the disclosure. All directional references (e.g., distal, proximal, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A medical device comprising:
a disk-shaped portion having a distal end and a proximal end and configured to isolate a portion of a ventricular wall, the disk-shaped portion having a contracted state when constrained within a delivery device and a preset, expanded state when deployed from the delivery device, wherein the disk-shaped portion is formed from a tubular structure comprising a plurality of braided strands, and the disk-shaped portion comprises a center member disposed on the proximal end thereof, the center member securing proximal ends of the plurality of braided strands of the disk-shaped portion at the proximal end of the disk-shaped portion; and an anchor coupled to the distal end of the disk-shaped portion and configured to secure the medical device to the ventricular wall, wherein, when the disk-shaped portion is in the expanded state, the disk-shaped portion has a tapered cone shape that increases in diameter from the distal end of the disk-shaped portion to a proximal-most surface of the proximal end of the disk-shaped portion.

2. The medical device of claim 1, wherein the center member is configured to engage the delivery device.

3. The medical device of claim 1, wherein the anchor is configured to extend partially into the ventricular wall distally away from the distal end.

4. The medical device of claim 3, wherein the anchor comprises a screw.

5. The medical device of claim 3, wherein the anchor comprises at least one barb for securing the medical device to the ventricular wall.

6. The medical device of claim 1, wherein the anchor is configured to extend from an inner surface of the ventricular wall to an outer surface of the ventricular wall.

7. The medical device of claim 6, wherein the anchor comprises a self-expanding anchoring member having a contracted state when constrained within the delivery device and a preset, expanded state when deployed from the delivery device.

8. The medical device of claim 7, wherein the self-expanding anchoring member comprises a disk-shaped portion configured for deployment adjacent the outer surface of the ventricular wall and a reduced diameter portion configured for deployment within the ventricular wall.

9. The medical device of claim 6, wherein the anchor comprises a positioning member configured for deployment adjacent the outer surface of the ventricular wall and a tethering member coupling the disk-shaped portion to the positioning member and configured to extend through the ventricular wall.

10. The medical device of claim 6, wherein the anchor comprises a plug having a first portion configured for deployment adjacent the outer surface of the ventricular wall and a reduced-diameter portion configured to extend through the ventricular wall.

11. The medical device of claim 1, wherein the disk-shaped portion further includes a membrane or coating thereon.

12. The medical device of claim 11, wherein the membrane or coating comprises polyester.

13. The medical device of claim 1, wherein the disk-shaped portion has a convex curvature proximate to the center member.

14. The medical device of claim 1, wherein the disk-shaped portion has a concave curvature proximate to the anchor.

\* \* \* \* \*